(12) United States Patent
Showell et al.

(10) Patent No.: US 10,252,928 B2
(45) Date of Patent: *Apr. 9, 2019

(54) METHOD FOR REDUCING CYANURIC ACID IN RECREATIONAL WATER SYSTEMS

(71) Applicant: BIOWISH TECHNOLOGIES, INC., Cincinnati, OH (US)

(72) Inventors: Michael S. Showell, Cincinnati, OH (US); Richard S. Carpenter, West Chester, OH (US); John Gorsuch, Cincinnati, OH (US); Joseph Roberts, Cincinnati, OH (US); David Bartoli, Murrieta, CA (US); Richard Rosene, Murrieta, CA (US); Lora Rosene, Murrieta, CA (US)

(73) Assignee: BiOWiSH Technologies, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/522,170

(22) PCT Filed: Nov. 2, 2015

(86) PCT No.: PCT/US2015/058593
§ 371 (c)(1),
(2) Date: Apr. 26, 2017

(87) PCT Pub. No.: WO2016/070174
PCT Pub. Date: May 6, 2016

(65) Prior Publication Data
US 2017/0334757 A1    Nov. 23, 2017

Related U.S. Application Data

(63) Continuation of application No. 14/633,664, filed on Feb. 27, 2015, now Pat. No. 9,302,924.
(Continued)

(51) Int. Cl.
C02F 3/34 (2006.01)
C12N 1/20 (2006.01)
(Continued)

(52) U.S. Cl.
CPC .............. *C02F 3/341* (2013.01); *C12N 1/20* (2013.01); *C02F 2101/16* (2013.01);
(Continued)

(58) Field of Classification Search
CPC .......................... C02F 3/341; C02F 2101/38; C02F 2303/185; C02F 2103/42; C02F 2305/06; C12N 1/20
(Continued)

(56) References Cited

U.S. PATENT DOCUMENTS

| | | | |
|---|---|---|---|
| 5,627,069 A | 5/1997 | Powlen | |
| 6,025,152 A | 2/2000 | Hiatt | |

(Continued)

FOREIGN PATENT DOCUMENTS

| | | |
|---|---|---|
| CN | 101473896 A | 7/2009 |
| CN | 101503664 A | 8/2009 |

(Continued)

OTHER PUBLICATIONS

International Search Report from corresponding PCT Application No. PCT/US2015/058593, dated Feb. 8, 2016.
(Continued)

*Primary Examiner* — Fred Prince
(74) *Attorney, Agent, or Firm* — Cooley LLP; Ivor R. Elrifi; Cynthia A. Kozakiewicz

(57) ABSTRACT

The present invention provides compositions and methods of reducing cyanuric acid levels in recreational water systems.

13 Claims, 10 Drawing Sheets

Specification includes a Sequence Listing.

Related U.S. Application Data

(60) Provisional application No. 62/073,335, filed on Oct. 31, 2014, provisional application No. 62/101,741, filed on Jan. 9, 2015.

(51) Int. Cl.
  C02F 101/38    (2006.01)
  C02F 103/42    (2006.01)
  C02F 101/16    (2006.01)

(52) U.S. Cl.
  CPC ...... C02F 2101/38 (2013.01); C02F 2103/42 (2013.01); C02F 2303/18 (2013.01); C02F 2303/185 (2013.01); C02F 2305/06 (2013.01)

(58) Field of Classification Search
  USPC ............ 210/167.11, 601, 610, 611, 615; 252/175; 435/174, 176, 177, 178, 179, 435/243, 252.31, 252.5, 262, 262.5
  See application file for complete search history.

(56) References Cited

U.S. PATENT DOCUMENTS

| | | |
|---|---|---|
| 6,410,305 B1 | 6/2002 | Miller et al. |
| 7,037,708 B1 | 5/2006 | Runge et al. |
| 9,302,924 B1 | 4/2016 | Showell et al. |
| 9,717,767 B2 * | 8/2017 | Carpenter ............... A61K 9/16 |
| 2003/0109025 A1 | 6/2003 | Durand et al. |
| 2004/0042972 A1 | 3/2004 | Truong-Le et al. |
| 2006/0188978 A1 | 8/2006 | Grant |
| 2007/0060477 A1 | 3/2007 | Pedersen et al. |
| 2007/0134493 A1 | 6/2007 | Meghpara |
| 2008/0260923 A1 | 10/2008 | Kratky et al. |
| 2009/0042267 A1 | 2/2009 | Park |
| 2009/0269307 A1 | 10/2009 | Albers |
| 2011/0014278 A1 | 1/2011 | Derrieu |
| 2011/0110894 A1 | 5/2011 | Drahos et al. |
| 2011/0269220 A1 | 11/2011 | Van Slyke |
| 2012/0083412 A1 | 4/2012 | Trevino et al. |
| 2012/0084886 A1 | 4/2012 | Lopez-Cervantes et al. |
| 2013/0337518 A1 | 12/2013 | Razavi-Shirazi et al. |
| 2014/0342437 A1 | 11/2014 | Carpenter |
| 2016/0029666 A1 | 2/2016 | Carpenter et al. |
| 2016/0312252 A1 | 10/2016 | Carpenter et al. |
| 2016/0326034 A1 | 11/2016 | Showell et al. |

FOREIGN PATENT DOCUMENTS

| | | |
|---|---|---|
| CN | 101538538 | 9/2009 |
| CN | 102399733 A | 4/2012 |
| CN | 102987079 A | 3/2013 |
| CN | 103484413 A | 1/2014 |
| CN | 103087918 B | 4/2015 |
| DE | 19617331 A1 | 11/1997 |
| EP | 0410877 A | 1/1991 |
| EP | 0720974 A1 | 7/1996 |
| GB | 2478929 A | 9/2011 |
| JP | 2001/299328 | 10/2001 |
| WO | WO 2001/068808 A1 | 9/2001 |
| WO | WO 2006/082328 A2 | 8/2006 |
| WO | WO 2009/038530 A1 | 3/2009 |
| WO | WO 2010/138522 A2 | 12/2010 |
| WO | WO 2014/189963 A1 | 11/2014 |
| WO | WO 2015/056185 A1 | 4/2015 |
| WO | WO 2016/019017 A1 | 2/2016 |
| WO | WO 2016/073981 A1 | 5/2016 |

OTHER PUBLICATIONS

Downes et al., "Complete nucleotide and deduced amino acid sequence of bovine phenylethanolamine N-methyltransferase: Partial amino acid homology with rat tyrosine hydroxylase", *Proc. Natl. Acad. Sci. USA*, 83: 5454-5458 (1984).

Downes et al., "Determination of Cyanuric Acid Levels in Swimming Pool Waters by u.v. Absorbance, HPLC and Melamine Cyanurate Precipitation," Water Res., vol. 18, No. 3, pp. 277-280 (1984).

O'Brien et al., "Equilibria in Aqueous Solutions of Chlorinated Isocyanurate", In *A.J. Rubin, ed. Chemistry of Water Supply, Treatment, and Distribution*, Chapter 14. Ann Arbor Science Publishers, Ann Arbor, Michigan (1974).

Shields et al., "Inactivation of Cryptosporidium parvum under chlorinated recreational water conditions", *Journal of Water and Health*, 06.4:513-5210 (2008).

Anonymous: "Biological Help for the Human Race Wastewater Treatment Solutions", 2011, pp. 1-12, Chicago, IL, USA.

Application Data Sheet 4950-01, Dissolved Oxygen Measurement in Wastewater Treatment, Water and Wastewater Industry, Emerson Process Management, http://www2.emersonprocess.com/siteadmincenter/PM%20Rosemount%20Analytical%20Documents/Liq_ADS_4950-01.pdf, 2009.

Baetge E. et al., "Complete nucleotide and deduced amino acid sequence of bovine phenylethanolamine N-methyltransferase: Partial amino acid homology with rat tyrosine hydroxylase," *Proceedings of the National Academy of Sciences* (1986) 83: 5454-5458.

Chan, Ada Mingwah "Investigation of Dairy Wastewater Using Biowish™", M. Sc. Thesis, (Dec. 2014), p. 1-142.

Deng, Bin et al. "The Denitrification Characteristics of Pseudomonas stutzeri SC221-M and its Application to Water Quality Control in Grass Carp Aquaculture", PLOS ONE, vol. 9, No. 12, (2014), p. e114886.

Encyclopedia of Food and Color Additives "Dextrose monohydrate. Soy lecithin" CRC Press (publisher). First edition (1997)CRC Press, Inc. Ed.: George A. Burdock, Ph.D., Boca Raton. FL., p. 1553-1554.

Gude et al. "Biodiesel from waste cooking oils via direct sonication", Applied Energy, vol. 109, (2013), pp. 135-144.

Hageman, J.H. et al. "Single, chemically defined sporulation medium for Bacillus subtilis; growth, sporulation, and extracellular protease production" Journal of Bacteriology, (1984), 160 (1), p. 438-441.

Hellinga, C. et al. "The Sharon process; An innovative method for nitrogen removal from ammonium-rich waste water", Water Science and Technology, (1998), 37 (9), p. 135-142.

Hommes, N.G. et al. "Chemolithoorganotrophic Growth of Nitrosomononas eruopaea on Fructose. Journal of Bacteriology", (2003), 185(23), p. 6809-6814.

Huang, Ting-Lin et al. "Nitrogen Removal from Micro-Polluted Reservoir Water by Indigenous Aerobic Denitrifiers" International Journal of Molecular Sciences, (2015), vol. 16, No. 4, pp. 8008-8026.

Jetten, M.S.M. et al. "Microbiology and application of the anaerobic ammonium oxidation ('anammox') process", Current Opinion in Biotechnology, (2001), 12 (3), p. 283-288.

Kim, J.K. et al. "Aerobic nitrification-denitrification by heterotrophic Bacillus strains", Bioresource Technology, (2005), 96(17), p. 1897-1906.

Koops, H. et al. "Distribution and ecophysiology of the nitrifying bacteria emphasizing cultured species", FEMS Microbiology Ecology, (2001), 37(1), p. 1-9.

Lee, Eva "Investigation of a Commerical Product (Biowish™) for Nitrogen Management", M. Sc. Thesis, May 2012, pp. 1-131.

Prosser, J.I., "Autotrophic nitrification in bacteria" Advances in microbial physiology, (1989), 30, p. 125-181.

Rajakumar, S. et al. "Nitrate removal efficiency of bacterial consortium (*Pseudomonas* sp. KW1 and *Bacillus* sp. YW4) in synthetic nitrate-rich water" Journal of Hazardous Materials, (2008), vol. 157, No. 2-3, p. 553-563.

Roberts, M.S. et al. "*Bacillus mojavensis* sp. nov., Distinguishable from Bacillus subtilis by Sexual Isolation, Divergence in DNA Sequence, and Differences in Fatty Acid Composition", International Journal of Systematic Bacteriology, (1994), vol. 44, No. 2, p. 256-264.

Sargent, M.G. "Control of cell length in Bacillus subtilis", Journal of Bacteriology (1975), 123(1), p. 7-19.

Schmidt, S.P. et al. "Reactions between dimanganese, dirhenium, and manganese-rhenium decacarbonyl and oxidants", Inorg. Chim. Acta, (1987), 131(2), p. 181-189.

(56) References Cited

OTHER PUBLICATIONS

Schmidt, I. et al. "New concepts of microbial treatment processes for the nitrogen removal in wastewater", FEMS Microbiology Reviews, (2003), p. 481-492.
Schreiber, F. "Detecting and Understanding Nitric Oxide Formation during Nitrogen Cycling in Microbial Biofilms" Dissertation, Universitaet Bremen, Bremen, (2009), 154 pages.
Shannon, M.A. et al. "Science and technology for water purification in the coming decades", Nature, (2008), 452, p. 301-310.
Shapleigh, J. "The Denitrifying Prokaryotes", The Prokaryotes (2006), 2, p. 769-792.
Strous, M. et al. "Missing lithotroph identified as new planctomycete", Nature (1999), 400, p. 446-449.
Third, K.A. et al. "The CANON system (Completely Autotrophic Nitrogen-removal Over Nitrite) under ammonium limitation; Interaction and competition between three groups of bacteria", Systematic and applied microbiology, (2001), 24 (4), p. 588-596.
Tramper, J. et al. "Operating performance of Nitrobacter agilis immobilized in carrageenan", Enzyme and Microbial Technology (1986), 8 (8), p. 477-480.
Veljković et al. "Biodiesel production by ultrasound-assisted transesterification: State of the art and the perspectives" Renewable and Sustainable Energy Reviews, (2012), vol. 16, p. 1193-1209.
Verbaendert, I. et al. "Denitrification is a common feature among members of the genus *Bacillus*", Syst Appl Microbio (2011), 34(5), p. 385-391.
Wang, Pan et al. "Isolation and immobilization of new aerobic denitrifying bacteria", International Biodeterioration and Biodegradation, (2012), vol. 76, Jul. 9, p. 12-17.
Studies on Screening and Characterization of Microorganisms with high Organic-Pollutants-Degrading Capability from Sea Cucumber (Apostichopus japonicus Selenka) Culture Ponds, Jun. 15, 2011, 12 pages.

* cited by examiner

Day 0

Day 1

Day 2

Results of Florida Field Trials

| | Pool #1 | Pool #2 | Pool #3 |
|---|---|---|---|
| Temperature | 60F | 65F | 55F |
| Dosage of Composition B (ppm) | 2.2 | 3.0 ppm | 3.0 ppm |
| Initial CYA Level (ppm) | 180 | >200 | >200 |
| CYA Level at 3 hrs (ppm) | 100 | 100 | 150 |
| CYA Level at 24 hrs (ppm) | 100 | 90 | 90 |

Fig. 9

Cyanuric Acid Reduction of Compositions A, B, and C Formulations

| Pool #1 | Pool #2 | Pool #3 |
|---|---|---|
| Product Dosage | Product Dosage | Product Dosage |
| 4.3 ppm Composition B | 3.7 ppm Composition A | 3.7 ppm Composition C |
| Pool Capacity = 14,000 gal. | Pool Capacity = 16,000 gal. | Pool Capacity = 16,000 gal. |
| 82°F | 80°F | 85°F |
| pH: 7.8 | pH: 7.6 | pH: 7.6 |
| Initial CYA level = +150 ppm | Initial CYA level = 120 ppm | Initial CYA level = 120 ppm |
| CYA level at 25 hours = 55 ppm | CYA level at 25 hours = 65 ppm | CYA level at 25 hours = 75 ppm |
| % CYA Reduction >63% | % CYA Reduction > 45% | % CYA Reduction > 37% |

1. Cyanuric Acid levels measured using standard test kit (precipitation method).

Fig. 10

SEQUENCE LISTING

```
<160> NUMBER OF SEQ ID NOS: 1

<210> SEQ ID NO 1
<211> LENGTH: 1668
<212> TYPE: DNA
<213> ORGANISM: Bacillus subtilis

<400> SEQUENCE: 1
agctcggatc cactagtaac ggccgccagt gtgctggaat tcgcccttag aaaggaggtg      60
atccagccgc accttccgat acggctacct tgttacgact tcaccccaat catctgtccc     120
accttcggcg gctggctcca taaaggttac ctcaccgact tcgggtgtta caaactctcg     180
tggtgtgacg ggcggtgtgt acaaggcccg ggaacgtatt caccgcggca tgctgatccg     240
cgattactag cgattccagc ttcacgcagt cgagttgcag actgcgatcc gaactgagaa     300
cagatttgtg rgattggctt aacctcgcgg tttcgctgcc ctttgttctg tccattgtag     360
cacgtgtgta gcccaggtca taaggggcat gatgatttga cgtcatcccc accttcctcc     420
ggtttgtcac cggcagtcac cttagagtgc ccaactgaat gctggcaact aagatcaagg     480
gttgcgctcg ttgcgggact taacccaaca tctcacgaca cgagctgacg acaaccatgc     540
accacctgtc actctgcccc cgaaggggac gtcctatctc taggattgtc agaggatgtc     600
```

-continued

```
aagacctggt aaggttcttc gcgttgcttc gaattaaacc acatgctcca ccgcttgtgc    660
gggcccccgt caattcctttt gagtttcagt cttgcgaccg tactccccag gcggagtgct   720
taatgcgtta gctgcagcac taaaggggcg gaaaccccct aacacttagc actcatcgtt   780
tacggcgtgg actaccaggg tatctaatcc tgttcgctcc ccacgctttc gctcctcagc   840
gtcagttaca gaccagagag tcgccttcgc cactggtgtt cctccacatc tctacgcatt   900
tcaccgctac acgtggaatt ccactctcct cttctgcact caagttcccc agtttccaat   960
gaccctcccc ggttgagccg ggggctttca catcagactt aagaaaccgc ctgcgagccc  1020
tttacgccca ataattccgg acaacgcttg ccacctacgt attaccgcgg ctgctggcac  1080
gtagttagcc gtggctttct ggttaggtac cgtcaaggtg ccgccctatt tgaacggcac  1140
ttgttcttcc ctaacaacag agctttacga tccgaaaacc ttcatcactc acgcggcgtt  1200
gctccgtcag actttcgtcc attgcggaag attccctact gctgcctccc gtaggagtct  1260
gggccgtgtc tcagtcccag tgtggccgat caccctctca ggtcggctac gcatcgtcgc  1320
cttggtgagc cgttacctca ccaactagct aatgcgccgc gggtccatct gtaagtggta  1380
gccgaagcca ccttttatgt ctgaaccatg cggttcagac aaccatccgg tattagcccc  1440
ggtttcccgg agttatccca gtcttacagg caggttaccc acgtgttact cacccgtccg  1500
ccgctaacat cagggagcaa gctcccatct gtccgctcga cttgcatgta ttaggcacgc  1560
cgccagcgtt cgtcctgagc catgaacaaa ctctaagggc gaattctgca gatatccatc  1620
acactggcgg ccgctcgagc atgcatctag agggcccaat cgccctat              1668
```

METHOD FOR REDUCING CYANURIC ACID IN RECREATIONAL WATER SYSTEMS

RELATED APPLICATIONS

This application is a national stage entry of PCT Application No. PCT/US2015/058593, filed on Nov. 2, 2015, which is a continuation of U.S. application Ser. No. 14/633,664, filed on Feb. 27, 2015, now U.S. Pat. No. 9,302,924, which claims priority to and benefit of U.S. Provisional Application No. 62/073,335, filed in Oct. 31, 2014, and U.S. Provisional Application No. 62/101,741, filed on Jan. 9, 2015, the contents of each of which are hereby incorporated by reference in their entireties.

INCORPORATION-BY-REFERENCE OF SEQUENCE LISTING

The contents of the text file named "BIOW-013-001WO-Sequence Listing-ST25.txt", which was created on Oct. 30, 2015 and is 3 KB in size, are hereby incorporated by reference in their entireties.

FIELD OF THE INVENTION

The present invention relates to a method for treating recreational water systems with compositions comprising an oxidizable carbon source and micro-organisms, in order to reduce cyanuric acid levels in said water systems.

BACKGROUND OF THE INVENTION

Recreational water systems such as swimming pools, spas, hot tubs, and jetted tubs, are commonly treated with chlorinated derivatives of cyanuric acid (1,3,5-triazine-2,4,6(1H,3H,5H)-trione) in order to disinfect the water and maintain sanitary conditions. The action of these chlorinated cyanuric acid derivatives, typically referred to by the trade names di- or trichlor, is attributed to the generation of free chlorine as HOCl and OCl-arising from the hydrolytic equilibria of the various chlorinated species (O'Brien et al., 1974). When used in this way there is a gradual accumulation of residual cyanuric acid in the water (Downes et al., 1984). As the level of cyanuric acid rises, free chlorine's ability to act as a disinfectant is weakened due to increased complexation of chlorine. Above about 50 ppm cyanuric acid, the time it takes to kill bacteria in chlorinated water increases versus similarly treated water without cyanuric acid. In heated systems, such as hot tubs and spas, at even moderate levels of cyanuric acid the amount of time it takes chlorine to kill a common pathogen such as *pseudomonas aeruginosa* can be as much as one hundred times as long as similar systems without cyanuric acid.

A 2007 study by the United States Centers for Disease Control and Prevention (Shields et al., 2007) revealed that cyanuric acid significantly diminishes chlorine's ability to inactivate chlorine-resistant porotozoan and *cryptosporidium*. Based on these findings several state and local Departments of Health have issued recommendations to the recreational water industry that cyanuric acid levels not exceed 30 ppm.

It is a common practice in the recreational water industry to reduce excess cyanuric acid levels by partially draining pools, tubs, spas, holding tanks, etc., and refilling with fresh water. This is a labor intensive and costly solution, particularly in areas affected by prolonged drought such as Southern California where the cost to replenish a typical 20,000 gallon swimming pool with fresh water is prohibitively high. Accordingly, a need exists in the recreational water industry for compositions and methods to reduce excess cyanuric acid levels that do not require a draining and replenishing

SUMMARY OF THE INVENTION

The invention provides compositions comprising a mixture of *Bacillus* bacterial species and a mixture of *Lactobacillus* bacterial species. The compositions can further comprise an oxidizable carbon source such as dextrose (e.g., anhydrous or monohydrate) or maltodextrin. The compositions of the invention can be used to reduce cyanuric acid in, e.g., recreational water systems.

In some embodiments, the mixture of *Bacillus* bacterial species in the composition includes *Bacillus subtilis*, *Bacillus licheniformis*, *Bacillus amyloliquefaciens*, and *Bacillus pumilus*. In some embodiments, the *Bacillus subtilis* can include one or more subspecies such as *Mojavensis* and *Bacillus subtilis* 34 KLB. In some embodiments, each of the *Bacillus* species are individually fermented aerobically, dried and ground, e.g., to an average particle size of about 200 microns. In some embodiments, the bacterial concentration of the *Bacillus* mixture is at least $1 \times 10^6$ colony forming units (CFU) per gram.

In some embodiments, the mixture of *Lactobacillus* bacterial species can include *Pediococcus acidilactici*, *Pediococcus pentosaceus*, and *Lactobacillus plantarum*. In some embodiments, each of the *Lactobacillus* species are fermented anaerobically, dried, and ground, e.g., to an average particle size of about 200 microns. In some embodiments, the bacterial concentration the *Lactobacillus* mixture is at least $1 \times 10^6$ colony forming units (CFU) per gram.

In one aspect, the invention relates to a composition comprising (a) between 75-99% w/w of anhydrous dextrose or dextrose monohydrate; (b) a mixture of *Bacillus* bacterial species comprising *Bacillus subtilis*, *Bacillus licheniformis*, *Bacillus amyloliquefaciens*, and *Bacillus pumilus* having a bacterial concentration of at least $1 \times 10^6$ colony forming units (CFU) per gram of the mixture, wherein each of the *Bacillus* species are individually fermented aerobically, dried and ground to an average particle size of about 200 microns, and wherein the *Bacillus subtilis* comprises *Mojavensis* and *Bacillus subtilis* 34 KLB; and (c) a mixture of *Lactobacillus* bacterial species comprising *Pediococcus acidilactici*, *Pediococcus pentosaceus*, and *Lactobacillus plantarum* having a bacterial concentration of at least $1 \times 10^6$ colony forming units (CFU) per gram of the mixture, wherein each of the *Lactobacillus* species are fermented anaerobically, dried, and ground to an average particle size of about 200 microns.

In another aspect, the invention relates to a composition comprising (a) between 75-95% w/w of anhydrous dextrose or dextrose monohydrate; (b) at least 1% w/w of a mixture containing *Bacillus* bacterial species comprising *Bacillus subtilis*, *Bacillus licheniformis*, *Bacillus amyloliquefaciens*, and *Bacillus pumilus*, wherein each of the *Bacillus* species are individually fermented aerobically, dried and ground to an average particle size of about 200 microns, and wherein the *Bacillus subtilis* comprises *Mojavensis* and *Bacillus subtilis* 34 KLB; and (c) at least 4% w/w of a mixture containing *Lactobacillus* bacterial species comprising *Pediococcus acidilactici*, *Pediococcus pentosaceus*, and *Lactobacillus plantarum*, wherein each of the *Lactobacillus* species are fermented anaerobically, dried, and ground to an average particle size of about 200 microns.

In a preferred embodiment the invention provides a composition comprising at least 0.4% w/w/ of a first *Bacillus* mixture comprising *Bacillus subtilis* subsp *mojavensis, Bacillus licheniformis, Bacillus amyloliquefaciens,* and *Bacillus pumilus*; at least 0.4% w/w/ of a second *Bacillus* mixture comprising *Bacillus subtilis, Bacillus licheniformis, Bacillus amyloliquefaciens,* and *Bacillus pumilus*; at least 0.4% w/w/ of a mixture of *Bacillus subtilis* 34 KLB; and at least 4% w/w of a *Lactobacillus* mixture comprising *Pediococcus acidilactici, Pediococcus pentosaceus,* and *Lactobacillus plantarum*. The remainder of the composition comprise an oxidizable carbon source such as anhydrous dextrose or dextrose monohydrate. The *Lactobacillus* in the *Lactobacillus* mixture are present in equal proportions by weight. The *Bacillus subtilis* subsp *mojavensis,* the *Bacillus amyloliquefaciens,* and the *Bacillus pumilus* in the first *Bacillus* mixture are present in equal proportions by weight.

In yet another aspect, the invention relates to a method of reducing cyanuric acid concentration on recreational water systems comprising contacting a pool's filtration system with the composition of the invention.

In some embodiments of any one of the aforementioned aspects, the bacterial species are non-pathogenic.

In some embodiments of any one of the aforementioned aspects, at least 15% of the *Bacillus* bacterial species are *Bacillus subtilis* 34 KLB.

In some embodiments of any one of the aforementioned aspects, each of the *Lactobacillus* bacterial species is present in equal amounts by weight.

In some embodiments of any one of the aforementioned aspects, the composition further comprises an inorganic mineral that stimulates bacterial respiration and growth. Non-limiting examples of inorganic minerals include disodium hydrogen phosphate, dipotassium hydrogen phosphate, sodium dihydrogen phosphate, potassium dihydrogen phosphate, sodium chloride, potassium chloride, magnesium sulfate, calcium sulfate, magnesium chloride, calcium chloride, and iron(III) chloride.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIG. 9 shows the results from Florida field trials using Composition B from Example 1.

FIG. 10 shows the results comparing Compositions A, B, and C from Example 1 in actual swimming pools.

DETAILED DESCRIPTION OF THE INVENTION

Figure 1:
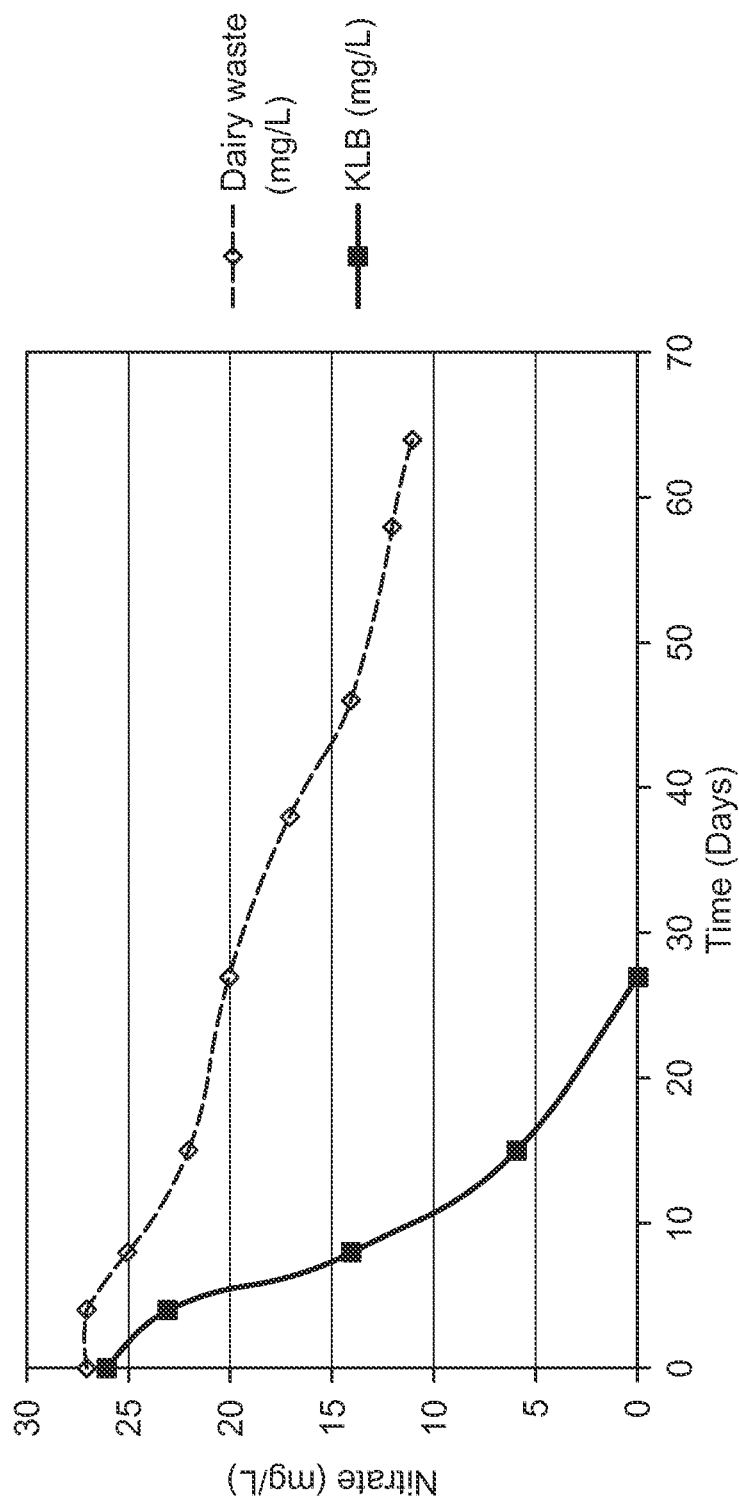
FIG. 1 is a graph showing significant denitrification was observed within the first 24 hours of dosing the water with the composition of the invention.

The invention provides compositions and methods for augmenting the treatment of commercial, public, and private recreational water systems such as swimming pools, spas, hot tubs, jetted tubs or the like. The composition and methods can result in increased clarity of the water, decreased nitrate concentrations, decreased cyanuric acid levels, decreased biological oxygen demand (BOD), decreased total suspended solids (TSS), decreased total Kjeldahl nitrogen (TKN) and decreased fats, oils and grease (FOG) in the water. In specific embodiments, the compositions and methods are used to reduce cyanuric acid levels in recreational water systems where cyanuric acid stabilized chlorine is used as part of the routine disinfection and sanitization protocol.

The microbes used in the product according to the present invention may be any conventional mesophilic bacteria. It is preferred that the bacteria are selected from the Lactobacillacae and Bacillaceae families. More preferably the bacteria selected from the genre *Bacillus* and *Lactobacillus* are included in the compositions of the invention.

In some aspects the compositions are microbial compositions. The microbial compositions are in powdered, dried form. Alternatively, the microbial compositions are in liquid form. For example, the composition includes non-pathogenic bacteria with the ability to degrade cyanuric acid.

In certain embodiments the bacteria are derived from the genus *Bacillus, Lactobacillus, Pseudomonas,* or *Moorella*. In other aspects the microbial compositions contain a mixture of *Bacillus* and *Lactobacillus* bacteria. In various aspects the mixture contains at least one to seven different strains of *Bacillus*. The mixture contains at least one to four different strains of *Lactobacillus*. Optionally, the microbial compositions further include an oxidizable carbon source and/or a mixture of inorganic minerals commonly used to stimulate microbial growth.

Preferred strains of *Bacillus* include for example, *Bacillus subtilis, Bacillus amyloliquefaciens, Bacillus licheniformis, Bacillus pumilus, Bacillus megaterium, Bacillus coagulans,* or *Paenibacillus polymyxa*. Preferred *Lactobacillus* strains include for example, *Pediococcus acidilactici, Pediococcus pentosaceus, Lactobacillus plantarum,* or *Bifidobacterium animalis*.

In a preferred embodiment the *Bacillus* is subspecies *Mojavenis*. In particularly preferred embodiments, the *Bacillus* is *Bacillus subtilis* strain 34KLB (SEQ ID NO: 1):

Bacillus subtilis strain 34KLB
(SEQ ID NO: 1)
AGCTCGGATCCACTAGTAACGGCCGCCAGTGTGCTGGAATTCGCCCTTAG
AAAGGAGGTGATCCAGCCGCACCTTCCGATACGGCTACCTTGTTACGACT
TCACCCCAATCATCTGTCCCACCTTCGGCGGCTGGCTCCATAAAGGTTAC
CTCACCGACTTCGGGTGTTACAAACTCTCGTGGTGTGACGGGCGGTGTGT
ACAAGGCCCGGGAACGTATTCACCGCGGCATGCTGATCCGCGATTACTAG
CGATTCCAGCTTCACGCAGTCGAGTTGCAGACTGCGATCCGAACTGAGAA
CAGATTTGTGRGATTGGCTTAACCTCGCGGTTTCGCTGCCCTTTGTTCTG
TCCATTGTAGCACGTGTGTAGCCCAGGTCATAAGGGGCATGATGATTTGA
CGTCATCCCCACCTTCCTCCGGTTTGTCACCGGCAGTCACCTTAGAGTGC
CCAACTGAATGCTGGCAACTAAGATCAAGGGTTGCGCTCGTTGCGGGACT
TAACCCAACATCTCACGACACGAGCTGACGACAACCATGCACCACCTGTC
ACTCTGCCCCCGAAGGGGACGTCCTATCTCTAGGATTGTCAGAGGATGTC
AAGACCTGGTAAGGTTCTTCGCGTTGCTTCGAATTAAACCACATGCTCCA
CCGCTTGTGCGGGCCCCCGTCAATTCCTTTGAGTTTCAGTCTTGCGACCG
TACTCCCCAGGCGGAGTGCTTAATGCGTTAGCTGCAGCACTAAAGGGGCG
GAAACCCCCTAACACTTAGCACTCATCGTTTACGGCGTGGACTACCAGGG
TATCTAATCCTGTTCGCTCCCCACGCTTTCGCTCCTCAGCGTCAGTTACA
GACCAGAGAGTCGCCTTCGCCACTGGTGTTCCTCCACATCTCTACGCATT
TCACCGCTACACGTGGAATTCCACTCTCCTCTTCTGCACTCAAGTTCCCC
AGTTTCCAATGACCCTCCCCGGTTGAGCCGGGGCTTTCACATCAGACTT
AAGAAACCGCCTGCGAGCCCTTTACGCCCAATAAtTCCGGACAACGCTTG
CCACCTACGTATTACCGCGGCTGCTGGCACGTAGTTAGCCGTGGCTTTCT
GGTTAGGTACCGTCAAGGTGCCGCCCTATTTGAACGGCACTTGTTCTTCC
CTAACAACAGAGCTTTACGATCCGAAAACCTTCATCACTCACGCGGCGTT
GCTCCGTCAGACTTTCGTCCATTGCGGAAGATTCCCTACTGCTGCCTCCC
GTAGGAGTCTGGGCCGTGTCTCAGTCCCAGTGTGGCCGATCACCCTCTCA
GGTCGGCTACGCATCGTCGCCTTGGTGAGCCGTTACCTCACCAACTAGCT
AATGCGCCGCGGGTCCATCTGTAAGTGGTAGCCGAAGCCACCTTTTATGT
CTGAACCATGCGGTTCAGACAACCATCCGGTATTAGCCCCGGTTTCCCGG
AGTTATCCCAGTCTTACAGGCAGGTTACCCACGTGTTACTCACCCGTCCG
CCGCTAACATCAGGGAGCAAGCTCCCATCTGTCCGCTCGACTTGCATGTA
TTAGCACGCCGCCAGCGTTCGTCCTGAGCCATGAACAAACTCTAAGGGC
GAATTCTGCAGATATCCATCACACTGGCGGCCGCTCGAGCATGCATCTAG
AGGGCCCAATCGCCCTAT In some embodiments, at least 15% of the *Bacillus* bacterial species are *Bacillus subtilis* 34 KLB.

In some aspects the microbial composition comprises a mixture of *Bacillus subtilis, Bacillus amyloliquefaciens, Bacillus licheniformis*, and *Bacillus pumilus*. In another aspect the microbial composition comprises a mixture of *Pediococcus acidilactici, Pediococcus pentosaceus*, and *Lactobacillus plantarum*.

Suitable water soluble oxidizable carbon sources include carbohydrates, proteins, polysaccharides or mixtures thereof. In preferred embodiments the water soluble carbon source comprises glucose, dextrose, fructose, erythrose, arabinose, ribose, deoxyribose, galactose, mannose, sucrose, lactose, maltose, dextrin, maltodextrin, glycerol, sorbitol, xylitol, inulin, trehelose, low molecular weight starches, modified starches, cellobiose, modified celluloses, amino acids, water soluble peptides, or mixtures thereof.

In another aspect the composition contain containing an oxidizable carbon source and a mixture of inorganic minerals. The oxidizable carbon source is water soluble or water dispersible.

In some aspects the composition comprises at least 50%, preferably at least 75%, and most preferably at least 90% by weight of a water soluble or water dispersible oxidizable carbon source. In some embodiments the composition comprises at least 91%, 92%, 93%, 94%, 95%, 96%, 97%, 98%, or 99% by weight of a water soluble or water dispersible oxidizable carbon source. In some embodiments, the composition comprises 50%-99% by weight of a water soluble or water dispersible oxidizable carbon source. In some embodiments, the composition comprises 60%-99% by weight of a water soluble or water dispersible oxidizable carbon source. In some embodiments, the composition comprises 70%-99% by weight of a water soluble or water dispersible oxidizable carbon source. In some embodiments, the composition comprises 75%-99% by weight of a water soluble or water dispersible oxidizable carbon source. In some embodiments, the composition comprises 80%-99% by weight of a water soluble or water dispersible oxidizable carbon source.

Suitable water dispersible carbon sources include emulsified fats and oils. In certain preferred embodiments the water dispersible carbon source comprises soy lecithin, emulsified vegetable oil or mixtures thereof. Other embodiments include mixtures of water soluble and water dispersible oxidizable carbon sources.

In some embodiments, the composition further comprises an inorganic mineral that stimulates bacterial respiration and growth. Suitable minerals include disodium hydrogen phosphate, dipotassium hydrogen phosphate, sodium dihydrogen phosphate, potassium dihydrogen phosphate, sodium chloride, potassium chloride, magnesium sulfate, calcium sulfate, magnesium chloride, calcium chloride, and iron (III) chloride. The minerals comprise between 1 to 50%, 10 to 50%, 20 to 50%, 30 to 50% or 40 to 50% by weight of the composition. Preferably, the minerals comprise about 1%, 2%, 3%, 4%, 5%, 6%, 7%, 8%, 9%, 10%, 15%, 20%, 25%, 30%, 35%, 40%, 45%, 50% by weight of the composition.

A preferred composition according to the invention includes about 50% by weight of a water soluble or water dispersible oxidizable carbon source and about 50% by weight of a mixture of inorganic minerals. Preferably, the water soluble or water dispersible oxidizable carbon source is dextrose and the minerals include disodium hydrogen phosphate, dipotassium hydrogen phosphate, potassium dihydrogen phosphate, magnesium sulfate, calcium chloride, and iron(III) chloride.

Another preferred composition according to the invention includes at least 94% by weight of a water soluble or water dispersible oxidizable carbon source and the remainder by weight of a microbial mixture. The microbial mixture is a mixture of *Bacillus, Lactobacillus* or both. In some aspects the microbial composition comprises a mixture of *Bacillus subtilis, Bacillus amyloliquefaciens, Bacillus licheniformis* and *Bacillus pumilus*. In another aspect the microbial composition comprises *Bacillus subtilis, Bacillus amyloliquefa-*

*ciens, Bacillus licheniformis Bacillus pumilus, Pediococcus acidilactici, Pediococcus pentosaceus, Lactobacillus plantarum.*

A first preferred *Bacillus* mixture includes 10% by weight *Bacillus licheniformis*, 30% by weight *Bacillus pumilus*, 30% by weight *Bacillus amyloliquefaciens* and 30% by weight *Bacillus subtilis*. (referred to herein as *Bacillus* Mix #1). Preferably, the *Bacillus subtilis* in *Bacillus* Mix #1 is *Bacillus subtilis* subsp. *Mojavenis*

A second preferred *Bacillus* mixture includes equal weights of *Bacillus licheniformis, Bacillus pumilus, Bacillus amyloliquefaciens* and *Bacillus subtilis*. (referred to herein as *Bacillus* Mix #2). Preferably at least two strains of *Bacillus licheniformis* and *Bacillus subtilis* are present in *Bacillus* Mix #2)

A third preferred *Bacillus* mixture includes *Bacillus subtilis, Bacillus licheniformis, Bacillus amyloliquefaciens,* and *Bacillus pumilus*. In some embodiments, the *Bacillus subtilis* can include one or more subspecies such as *Mojavensis* and *Bacillus subtilis* 34 KLB.

A forth preferred *Bacillus* mixture includes *Bacillus subtilis* 34 KLB (*Bacillus* Mix #3)

A preferred *Lactobacillus* mixture includes equal weights of *Pediococcus acidilactici, Pediococcus pentosaceus, Lactobacillus plantarum*. (referred to herein as *Lactobacillus* Mix #1).

A preferred composition according to the invention includes at least 94% by weight of a water soluble or water dispersible oxidizable carbon source and about at least 0.1 to 1%, 0.1 to 2%, 0.1 to 3%, 0.1 to 4%, 0.1 to 5% of *Bacillus* Mix#1 and/or of *Bacillus* Mix#2. Preferably the composition comprises about 0.1%, 0.2%, 0.3%, 0.4%, 0.5%, 0.6%, 0.7%, 0.8%, 0.9% or 1% of *Bacillus* Mix#1 and/or of *Bacillus* Mix#2. In some embodiments the composition also includes about at least 0.1 to 1%, 0.1 to 2%, 0.1 to 3%, 0.1 to 4%, 0.1 to 5% of *Bacillus* 34KLB. Preferably the composition comprises about 0.1%, 0.2%, 0.3%, 0.4%, 0.5%, 0.6%, 0.7%, 0.8%, 0.9% 1%, 2%, 3%, 4% or 5% of *Bacillus* 34KLB.

In yet another preferred composition according to the invention includes at least 94% by weight of a water soluble or water dispersible oxidizable carbon source and about at least 0.1 to 1%, 0.1 to 2%, 0.1 to 3%, 0.1 to 4%, 0.1 to 5% of *Bacillus* Mix#1 and *Bacillus* Mix#2 and about at least 1 to 5% *Lactobacillus* Mix #1. Preferably the composition comprises about 0.1%, 0.2%, 0.3%, 0.4%, 0.5%, 0.6%, 0.7%, 0.8%, 0.9% or 1% of *Bacillus* Mix#1 and *Bacillus* Mix#2 and about 1%, 2%, 3% 4% or 5% of *Lactobacillus* Mix #1.

In another preferred composition according to the invention includes at least 94% by weight of a water soluble or water dispersible oxidizable carbon source and about at least 0.1%, 0.2%, 0.3%, 0.4%, or 0.5%, of *Bacillus* Mix#1; at least 0.1%, 0.2%, 0.3%, 0.4%, or 0.5% *Bacillus* Mix#2; about at least 1 to 5% *Lactobacillus* Mix #1 and 0.1%, 0.2%, 0.3%, 0.4%, 0.5%, *Bacillus* Mix#3.

In a more preferred composition according to the invention includes equal weights of *Bacillus* Mix#1, *Bacillus* Mix#2, *Bacillus* Mix#3 and at least 4% *Lactobacillus* Mix #1. The remainder of the composition being a non oxidizable carbon source such as anhydrous dextrose or dextrose monohydrate.

In another preferred composition according to the invention includes at least 0.4% *Bacillus* Mix#1, at least 0.4% *Bacillus* Mix#2, at least 0.4% *Bacillus* Mix#3 and at least 4% *Lactobacillus* Mix #1. The remainder of the composition being a non oxidizable carbon source such as anhydrous dextrose or dextrose monohydrate.

In some embodiments, the composition comprises (a) between 75-99% w/w of anhydrous dextrose or dextrose monohydrate; (b) a mixture of *Bacillus* bacterial species comprising *Bacillus subtilis, Bacillus licheniformis, Bacillus amyloliquefaciens,* and *Bacillus pumilus* having a bacterial concentration of at least $1 \times 10^6$ colony forming units (CFU) per gram of the mixture, wherein each of the *Bacillus* species are individually fermented aerobically, dried and ground to an average particle size of about 200 microns, and wherein the *Bacillus subtilis* comprises *Mojavensis* and *Bacillus subtilis* 34 KLB; and (c) a mixture of *Lactobacillus* bacterial species comprising *Pediococcus acidilactici, Pediococcus pentosaceus,* and *Lactobacillus plantarum* having a bacterial concentration of at least $1 \times 10^6$ colony forming units (CFU) per gram of the mixture, wherein each of the *Lactobacillus* species are fermented anaerobically, dried, and ground to an average particle size of about 200 microns.

In some embodiments, the composition comprises (a) between 75-95% w/w of anhydrous dextrose or dextrose monohydrate; (b) at least 1% w/w of a mixture containing *Bacillus* bacterial species comprising *Bacillus subtilis, Bacillus licheniformis, Bacillus amyloliquefaciens,* and *Bacillus pumilus*, wherein each of the *Bacillus* species are individually fermented aerobically, dried and ground to an average particle size of about 200 microns, and wherein the *Bacillus subtilis* comprises *Mojavensis* and *Bacillus subtilis* 34 KLB; and (c) at least 4% w/w of a mixture containing *Lactobacillus* bacterial species comprising *Pediococcus acidilactici, Pediococcus pentosaceus,* and *Lactobacillus plantarum*, wherein each of the *Lactobacillus* species are fermented anaerobically, dried, and ground to an average particle size of about 200 microns.

The levels of the bacteria to be used according to the present invention will depend upon the types thereof. It is preferred that the present product contains bacteria in an amount between about $10^5$ and $10^{11}$ colony forming units per gram.

The microbial compositions according to the invention may be produced using any standard fermentation process known in the art. For example, solid substrate or submerged liquid fermentation under conditions which are optimized for growth of each organism. The fermented cultures can be mixed cultures or single isolates.

Preferably, mixtures of bacteria are manufactured by individually aerobically or anaerobically fermenting each organism; harvesting each organism; drying the harvested organisms, grinding the dried organisms to produce a powder combining each of the organisms into the final mixture.

In some embodiments, the bacteria are anaerobically fermented in the presence of carbohydrates. Suitable carbohydrates include inulin, fructo-oligosaccharide, and gluco-oligosaccharides.

When the cell density of the fermentation reaches about $10^{11}$-$10^{12}$ cfu/g, the individual bacteria are harvested. The bacteria may be harvested by any known methods in the art. For example the bacteria are harvested by filtration or centrifugation.

The bacteria are dried by any method known in the art. For example the bacteria are air dried, or dried by freezing in liquid nitrogen followed by lyophilization.

The compositions according to the invention have been dried to moisture content less than 20%, 15%, 10% 9%, 8%, 7%, 6%, 5%, 4%, 3%, 2%, or 1%. Preferably, the composition according to the invention has been dried to moisture content less than 5%.

In some embodiments the dried powder is ground to decrease the particle size. The bacteria are ground by conical grinding at a temperature less than 10° C., 9° C., 8° C., 7° C., 6° C., 5° C., 4° C., 3° C., 1° C., 0° C., or less. Preferably the temperature is less than 4° C.

For example the particle size is less than 1500, 1400, 1300, 1200, 1100, 1000, 900, 800, 700, 600, 500, 400, 300, 200, or 100 microns. Preferably, the freeze dried powder is ground to decrease the particle size such that the particle size is less than 800 microns. Most preferred are particle sizes less than about 400 microns. In most preferred embodiments, the dried powder has a mean particle size of 200 microns, with 60% of the mixture in the size range between 100-800 microns. In various embodiments the freeze dried powder is homogenized.

In various embodiments the microbial compositions are mixed with an inert carrier such anhydrous dextrose, dextrose monohydrate, dendritic salt, rice bran, wheat bran, oat bran, soybean meal, rice hulls, or a mixture thereof.

The inert carrier is at a concentration of at least 60%, 70%, 75%, 80%, 85%, 90%, 95% or more. Preferably, the inert carrier is at a concentration of about between 75-95% (w/w).

In other aspects the bacterial compositions contain an organic emulsifier such as, for example, soy lecithin. The organic emulsifier is at a concentration of about 1%, 2%, 3%, 4%, 5%, 5, 7%, 8%, 9% or 10%. Preferably, the organic emulsifier is at a concentration of between 2 to 5% (w/w).

In other aspects the microbial compositions are mixed in equal proportion and added to an oxidizable carbon source. Typically, the final concentration of bacteria in the finished composition ranges from $10^5$ to $10^{11}$ cfu/g. In some embodiments, the final concentration of bacteria in the finished composition is at least $10^6$ cfu/g.

Further, if desired, the microbial compositions may be encapsulated to further increase the probability of survival; for example in a sugar matrix, fat matrix or polysaccharide matrix.

Importantly, the compositions of the invention fully disperses upon the addition to water and unlike other water treatment microbial compositions the compositions do not require a pre-activation of the bacteria prior to use.

The compositions of the invention can be used to treat both fresh and salt Ovate commercial, municipal, industrial, and residential swimming pools, spas, hot tubs, jetted tubs and the like.

An aqueous solution of the dry composition according to the invention can be employed to increase clarity of the water, decrease nitrate concentrations, cyanuric acid levels, biological oxygen demand (BOD), total suspended solids (TSS), total Kjeldahl nitrogen (TKN) and fats, oils and grease (FOG) in body of water. The compositions of the invention may also be used to treat swimming pools and the like to remove scum and reduce algae.

Preferably, the compositions of the invention can be used in methods to decrease the concentrations of cyanuric acid in recreational water systems such as swimming pools, spas, hot tubs, jetted tubs and the like. In some embodiments the compositions of the invention stimulates or augments the endogenous biofilm of the recreational water systems filter to break down the cyanuric acid.

Solutions of the composition can be pumped into the system to be treated or sprayed onto the surface, or into the airspace surrounding the material, or applied to a filter or other solid support through which the water to be cleaned is passed. The dry material can be mixed into a slurry or solution at the point of application and applied in a similar manner.

The invention includes methods for treating a recreational water system by contacting the water system with a composition having an oxidizable carbon source. The carbon source is water soluble or water dispersible. The method results in decreased cyanuric acid levels.

Solutions of the composition can be pumped into the system to be treated or sprayed onto the surface, or into the airspace surrounding the material, or applied to a filter or other solid support through which the water to be cleaned is passed. The dry material can be mixed into a slurry or solution at the point of application and applied in a similar manner.

The water system is dosed at a concentration range of about 0.01 to 100 ppm, preferably from 0.1 to 10 ppm.

In various aspects the invention provides compositions containing a mixture of micro-organisms for augmenting the treatment of swimming pool water. Importantly, the compositions of the invention fully disperse in water and do not require a pre-activation of the bacteria prior to use.

The compositions contain a mixture of *Bacillus* organisms or a mixture of *Bacillus* and *Lactobacillus*. In some embodiments the compositions contain *Bacillus subtilis, Bacillus amyloliquefaciens, Bacillus licheniformis, Bacillus pumilus, Bacillus megaterium, Bacillus coagulans,* or *Paenibacillus polymyxa*. In other embodiments the composition contains *Pediococcus acidilactici, Pediococcus pentosaceus, Lactobacillus plantarum,* or *Bifidobacterium animalis*

In preferred embodiments the mixture contains *Bacillus subtilis, Bacillus amyloliquefaciens, Bacillus licheniformis Bacillus pumilus* and *Pediococcus acidilactici, Pediococcus pentosaceus,* and *Lactobacillus plantarum*. In another preferred embodiment the mixture contains *Bacillus subtilis, Bacillus amyloliquefaciens, Bacillus licheniformis, Bacillus pumilus, Bacillus megaterium, Bacillus coagulans,* and *Paenibacillus polymyxa.*

Each of the organisms in the mixture is individually aerobically (*Bacillus*) or anaerobically (*Lactobacillus*) fermented, harvested, dried, and ground to produce a powder having a mean particle size of about 200 microns, with greater than about 60% of the mixture in the size range between 100-800 microns.

In some aspects the composition has a moisture content of less than about 5%; and a final bacterial concentration of about between $10^5$-$10^{11}$ colony forming units (CFU) per gram of the composition.

In various aspects the composition further contains an inert carrier such as anhydrous dextrose, dextrose monohydrate, dendritic salt, rice bran, wheat bran, oat bran, soybean meal, rice hulls, or a mixture thereof. Preferably, the inert carrier is at a concentration of about between 75-95% (w/w).

In other aspects the composition further includes an organic emulsifier. The organic emulsifier is for example, soy lecithin. Preferably, the organic emulsifier is at a concentration of about between 2 to 5% (w/w).

Also included in the invention are methods for treating the water in a swimming pool by contacting the water with a composition according to the invention. The method results in increased clarity of the water, decreased nitrate concentrations, decreased cyanuric acid levels, decreased biological oxygen demand (BOD), decreased total suspended solids (TSS), decreased total Kjeldahl nitrogen (TKN) and decreased fats, oils and grease (FOG) in the water.

In some aspects the water is contacted by contacting a swimming pool filtration unit with the composition. In other aspects the composition is imbedded in a solid support.

The terms "microbial", "bacteria" or microbes" as used herein, refer to micro-organisms that confer a benefit. The microbes according to the invention may be viable or non-viable. The non-viable microbes are metabolically-active. By "metabolically-active" as used herein is meant that they exhibit at least some respiration or residual enzyme, or secondary metabolite activity characteristic to that type of microbe.

By the term "non-viable" as used herein is meant a population of bacteria that is not capable of replicating under any known conditions. However, it is to be understood that due to normal biological variations in a population, a small percentage of the population (i.e. 5% or less) may still be viable and thus capable of respiration and/or replication under suitable growing conditions in a population which is otherwise defined as non-viable.

By the term "viable bacteria" as used herein is meant a population of bacteria that is capable of respirating and/or replicating under suitable conditions in which respiration and/or replication is possible. A population of bacteria that does not fulfill the definition of "non-viable" (as given above) is considered to be "viable".

The term "recreational water system" as used herein is meant to include swimming pools, spas, hot tubs, jetted tubs or the like, and includes both salt water and fresh water systems.

"Treating" as used herein means inoculating water with an oxidizable carbon source and/or microbes designed to enhance efficient degradation of organic matter, cyanuric acid or both.

The term "swimming pools" as used herein are meant to include swimming pools, spas, hot tubs or the like, and includes both salt water and fresh water systems.

Unless stated otherwise, all percentages mentioned in this document are by weight based on the total weight of the composition.

A better understanding of the present invention may be given with the following examples which are set forth to illustrate, but are not to be construed to limit the present invention.

EXAMPLES

Example 1: Preparation of the Microbial Species

The microbial species of the present invention may be made by any of the standard fermentation processes known in the art. In the following examples, both solid state and submerged liquid fermentation processes are described.

Solid State Fermentation—*Bacillus* Species

Individual purified isolates of *Bacillus subtilis, Bacillus amyloliquefaciens, Bacillus licheniformis, Bacillus pumilus, Bacillus megaterium, Bacillus coagulans*, and *Paenibacillus polymyxa* were grown-up in separate fermenters using standard aerobic submerged liquid fermentation protocols. The individual organisms were recovered from the fermenters via centrifugation, mixed together in equal proportions on a weight basis, then added to the following mixture: 1 part inulin, 2.2 parts isolated soy protein, 8 parts rice flour with 0.25% w/w sodium chloride, 0.045% w/w Calcium carbonate, 0.025% w/w Magnesium sulphate, 0.025% w/w Sodium phosphate, 0.012% w/w Ferrous sulphate and 29.6% water. This mixture was allowed to ferment for up to 5 days at 30° C. Upon completion of the fermentation, the entire mixture was freeze dried to a moisture content less than 5%, ground to an average particle size of 295 microns, with 60% of the product in the size range between 175-840 microns, and homogenized. The final microbial concentration of the powdered product is between $10^9$ and $10^{11}$ CFU/g.

Submerged Liquid Fermentation—*Bacillus* Species

Individual starter cultures of *Bacillus subtilis, Bacillus amyloliquefaciens, Bacillus licheniformis, Bacillus pumilus, Bacillus megaterium, Bacillus coagulans*, and *Paenibacillus polymyxa* are grown according to the following general protocol: 2 grams nutrient broth, 2 grams AmberFerm (yeast extract), and 4 grams Maltodextrin are added to a 250 ml Erlenmeyer flask. 100 milliliters distilled, deionized water was added and the flask stirred until all dry ingredients were dissolved. The flask was covered and placed for 30 min. in an Autoclave operating at 121° C. and 15 psi. After cooling, the flask was inoculated with 1 ml of one of the pure microbial strains. The flask was sealed and placed on an orbital shaker at 30° C. Cultures were allowed to grow for 3-5 days. This process was repeated for each of the micro-organisms in the mixture. This process provided starter cultures of each organism which were then used to prepare larger scale fermentations.

Individual fermenters were run under aerobic conditions at pH 7 at the temperature optimum for each species:

TABLE 1

| Microbe | Temperature Optimum |
| --- | --- |
| Bacillus subtilis | 35° C. |
| Bacillus amyloliquefaciens | 30° C. |
| Bacillus licheniformis | 37° C. |
| Bacillus coagulans | 37° C. |
| Bacillus megaterium | 30° C. |
| Bacillus pumilus | 32° C. |
| Paenibacillus polymyxa | 30° C. |

Solid State Fermentation—*Lactobacillus*

Individual purified isolates of *Pediococcus acidilactici, Pediococcus pentosaceus, Lactobacillus plantarum*, and *Bifidobacterium animalis* were grown-up in separate fermenters using standard anaerobic submerged liquid fermentation protocols. The individual organisms were recovered from the fermenters via centrifugation, mixed together in equal proportions on a weight basis, then added to the following mixture: 1 part inulin, 2.2 parts isolated soy protein, 8 parts rice flour with 0.25% w/w sodium chloride, 0.045% w/w Calcium carbonate, 0.025% w/w Magnesium sulphate, 0.025% w/w Sodium phosphate, 0.012% w/w Ferrous sulphate and 29.6% water. This mixture was allowed to ferment for up to 5 days at 30° C. Upon completion of the fermentation, the entire mixture was freeze dried to a moisture content less than 5%, ground to an average particle size of 295 microns, with 60% of the product in the size range between 175-840 microns, and homogenized. The final microbial concentration of the powdered product is between 109 and 1011 CFU/g.

Submerged Liquid Fermentation—*Lactobacillus*

Individual, purified isolates of *Pediococcus acidilactici, Pediococcus pentosaceus, Lactobacillus plantarum*, and *Bifidobacterium animalis* were grown-up in separate fermenters using standard anaerobic submerged liquid fermentation protocols. After fermentation the individual cultures were filtered, centrifuged, freeze dried to a moisture level less than about 5%, then ground to a mean particle size of 295 microns, with 60% of the product in a size range between 175-840 microns. The individual dried microbial cultures were then mixed in equal proportion by weight to obtain the microbial composition of the present invention. The final microbial concentration of the mixed powdered product is between $10^9$ and $10^{11}$ CFU/g.

Example 2: Formulation of Swimming Pool Treatment Products

The following formulations were prepared by dry blending the ingredients in a ribbon blender (all percentages are by weight):

TABLE 2

| Ingredients | COMPOSITIONS | | | | | | | |
|---|---|---|---|---|---|---|---|---|
| | A | B | C | D | E | F | G | H |
| Microbial Composition from Example 1 | 5 | 5 | 10 | 10 | 25 | 25 | | |
| Bacillus subtilis 34KLB produced via submerged liquid fermentation according to Example 1 B | | | | | | | 1 | 10 |
| Monohydrate Dextrose | 95 | | 90 | | 75 | | 99 | 90 |
| Nutri-Sure ™ | | 95 | | 90 | | 75 | | |

Example 3: Denitrification of Swimming Pool Water

The composition of Example 2H was used to reduce the nitrate level in a swimming pool. 100 grams of the composition of Example 2H were added to the skimmer of a 15,000 gallon swimming pool with initial nitrate level of about 25 ppm. Significant denitrification was observed within the first 24 hours of dosing. See FIG. 1.

Example 4: Water Clarification

Figure 2:
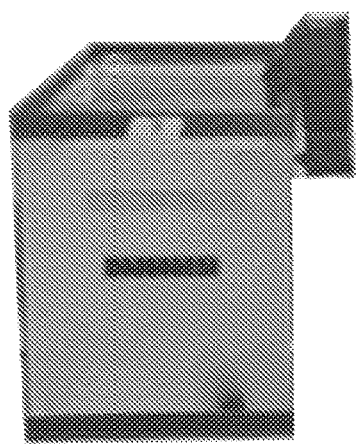
FIG. 2 is a series of figures showing increased water clarity after dosing the water with the composition of the invention.
Figure 2:
Figure 2:
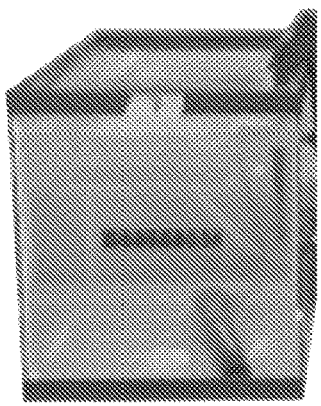

The conditions of a typical swimming pool (chlorine level, temperature) were mimicked in the laboratory using 10 gallon aquaria fitted with a filter and circulation pump. The composition of Example 2F was evaluated for its ability to clarify the water after addition of 250 ppm Sunscreen. Results are in FIG. 2.

Significant clarification is noted in as little as 24 hours. Separate respirometer analysis with sunscreen as a substrate showed significant CO2 generation and O2 consumption when the composition of Example 2F is added.

Example 5: Biodegradation of Cyanuric Acid

Figure 3:
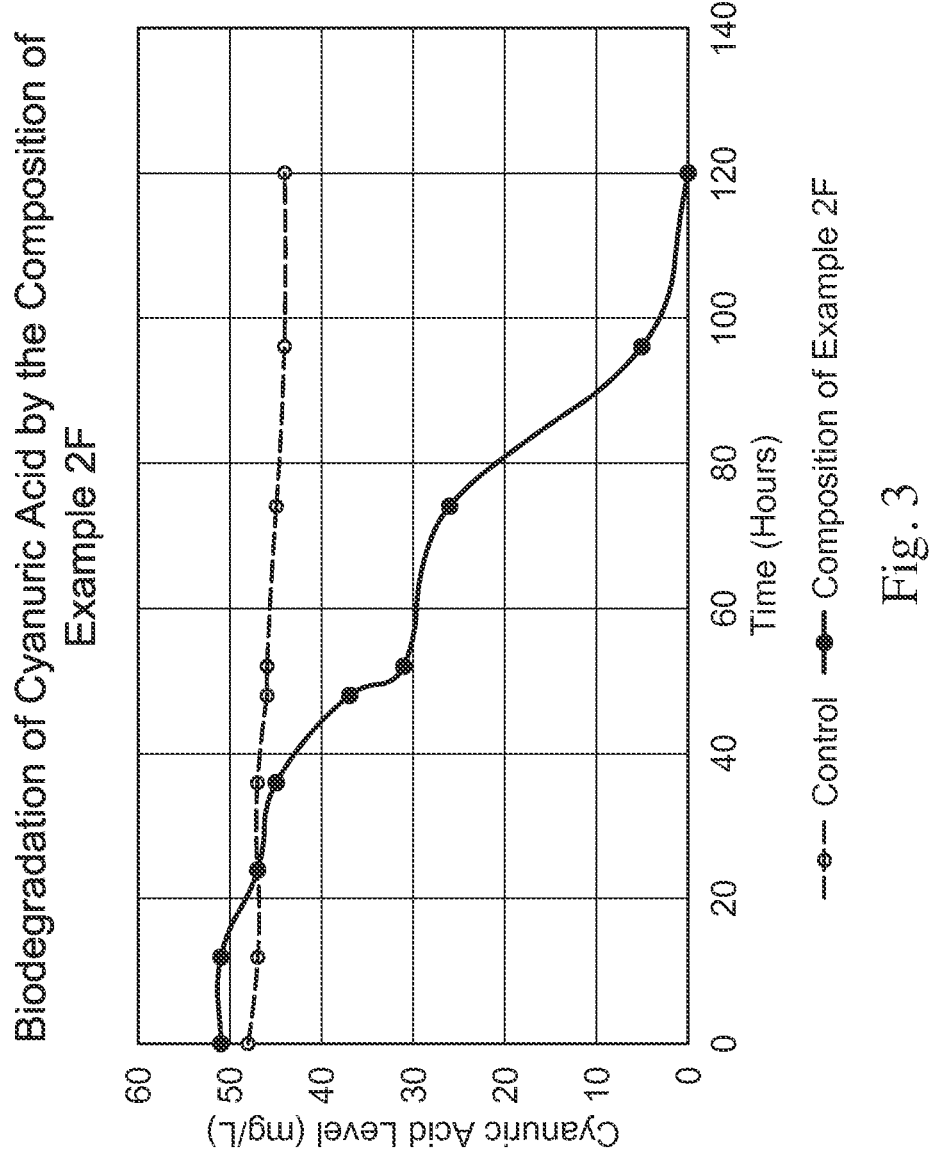
FIG. 3 is a graph showing decreased cyanuric acid with the composition of the invention.

The composition of Example 2E was evaluated for its ability to degrade cyanuric acid. A solution of 1 gram of the composition of Example 2E in 1 L of Deionized Water was prepared and allowed to stand for 40 hours at room temperature. 5 ml of this solution were then added to 500 ml of water containing minimal media and 50 ppm cyanuric acid. The degradation of cyanuric acid was followed by HPLC. Results are shown in FIG. 3.

Example 6: Cyanuric Acid Control in Swimming Pools

The composition of Example 2E was evaluated in swimming pool applications. Testing was conducted in 6 fresh water swimming pools and 3 salt water pools in Southern California. 100 grams of the composition of Example 2E were added to each pool and the cyanuric acid level determined as a function of time using a commercially available cyanuric acid test kit. Results are summarized in Table 3:

TABLE 3

| Cyanuric Acid Control in Swimming Pools | | | |
|---|---|---|---|
| | Cyanuric Acid at T = 0 | Cyanuric Acid at 1 week | % Reduction |
| Fresh Water Pool | | | |
| Pool #1 | 100 ppm | 57.5 ppm | 42.5 |
| Pool #2 | 100 ppm | 65 ppm | 35 |
| Pool #3 | 50 ppm | 20 ppm | 60 |
| Pool #4 | 100 ppm | 67.5 ppm | 32.5 |
| Pool #5 | >125 ppm | 100 ppm | >20 |
| Pool #6 | 100 ppm | 65 ppm | 35 |
| Salt Water Pool | | | |
| Pool #1 | >100 ppm | 40 ppm | >60 |
| Pool #2 | >200 ppm | 60 ppm | >70 |
| Pool #3 | >500 ppm | 120 ppm | >75 |

Example 7. Preparation of Cyanuric Acid Reducing Compositions

The following compositions were prepared (all percentages are by weight):

TABLE 4

| | Composition A | Composition B | Composition C | Composition D | Composition E | Composition F |
|---|---|---|---|---|---|---|
| Dextrose | 100% | 94.30% | 95.0% | 97.0% | | 50% |
| Maltodextrin | | | | | 94.0% | |
| Bacillus Mix #1 | | 0.43% | | 1.0% | 0.44% | |
| Bacillus Mix #2 | | 0.43% | | 1.0% | 0.44% | |
| Lactobacillus Mix #1 | | 4.40% | | | 4.40% | |
| B. Subtilis 34KLB | | 0.44% | 5.0% | 1.0% | 0.72% | |
| Mineral Mix | | | | | | 50% |

Where Bacillus Mix #1 comprises 10% by weight Bacillus licheniformis, 30% by weight Bacillus pumilus, 30% by weight Bacillus amyloliquefaciens, and 30% by weight Bacillus subtilis subspecies Mojavensis and has an activity ≥$10^{11}$ cuf/g; Bacillus Mix #2 comprises equal weights of Bacillus licheniformis, Bacillus pumilus, Bacillus amyloliquefaciens, and Bacillus subtilis with an activity ≥$10^9$ cfu/g; and, Lactobacillus Mix #1 comprises equal weights of

*Pediococcus acidilactici*, *Pediococcus pentosaceus*, and *Lactobacillus plantarum* at a concentration ≥$10^{10}$ cfu/g. The *Bacillus subtilis* 34KLB had an activity ≥$10^{10}$ cfu/g.

The mineral mix comprises the following:

TABLE 5

| Mineral | Wt. % |
|---|---|
| KH2PO4 | 12% |
| K2HPO4 | 31% |
| Na2HPO4*2H2O | 48% |
| CaCl2*2H2O | 5% |
| MgSO4*7H2O | 3% |
| FeCl3*6H2O | 1% |

Example 8. In Vitro Cyanuric Acid Reduction

Figure 4:
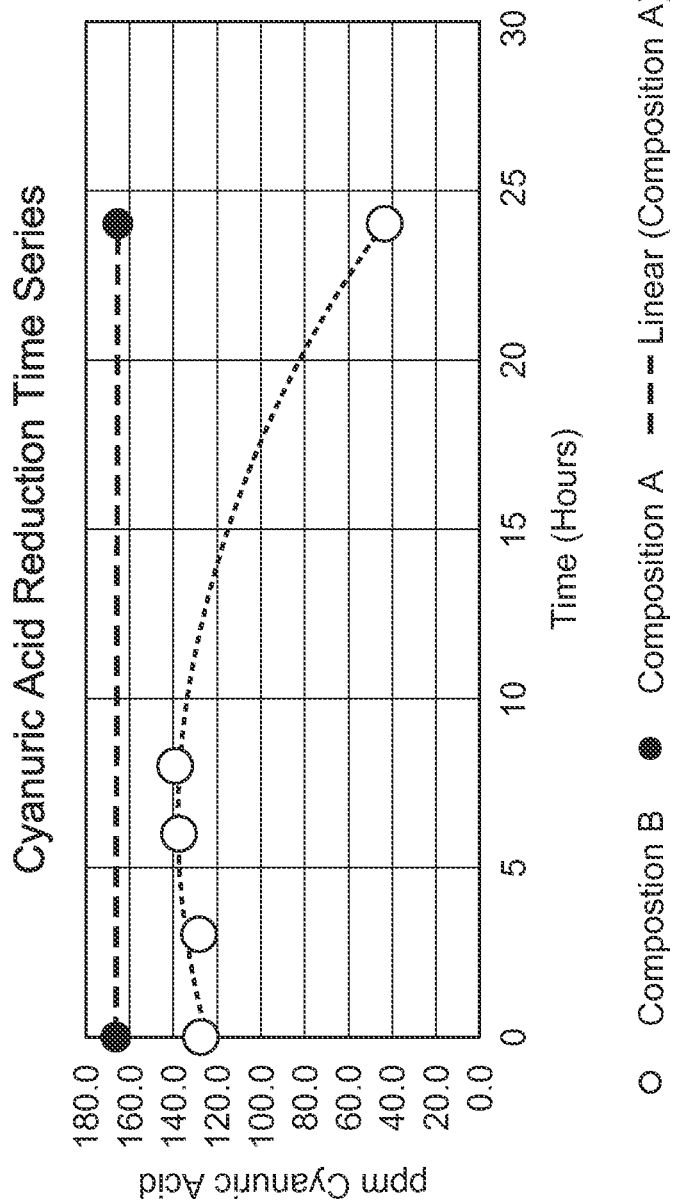
FIG. 4 shows results from MS-MS analysis of in-vitro samples of cyanuric acid treated with the compositions of the invention.
Figure 5:
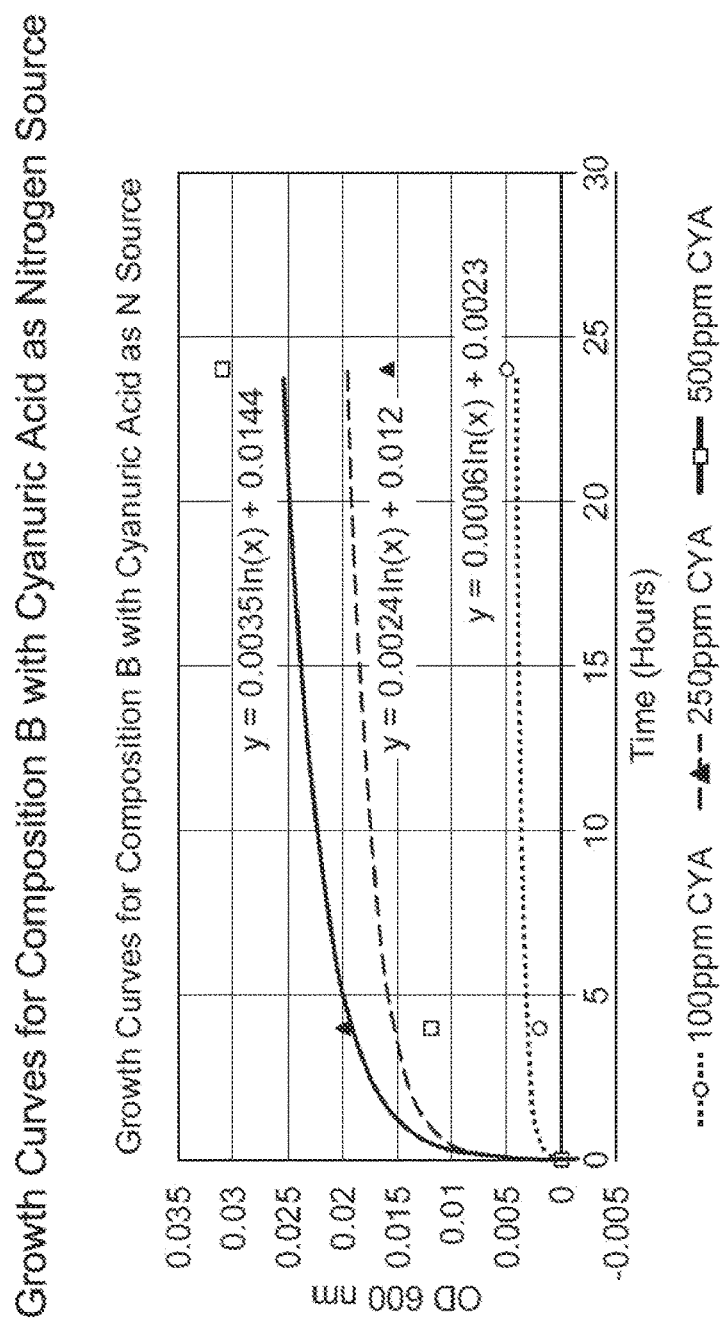
FIG. 5 are growth curves showing that organisms can use cyanuric acid as a nitrogen source for growth.
Figure 6:
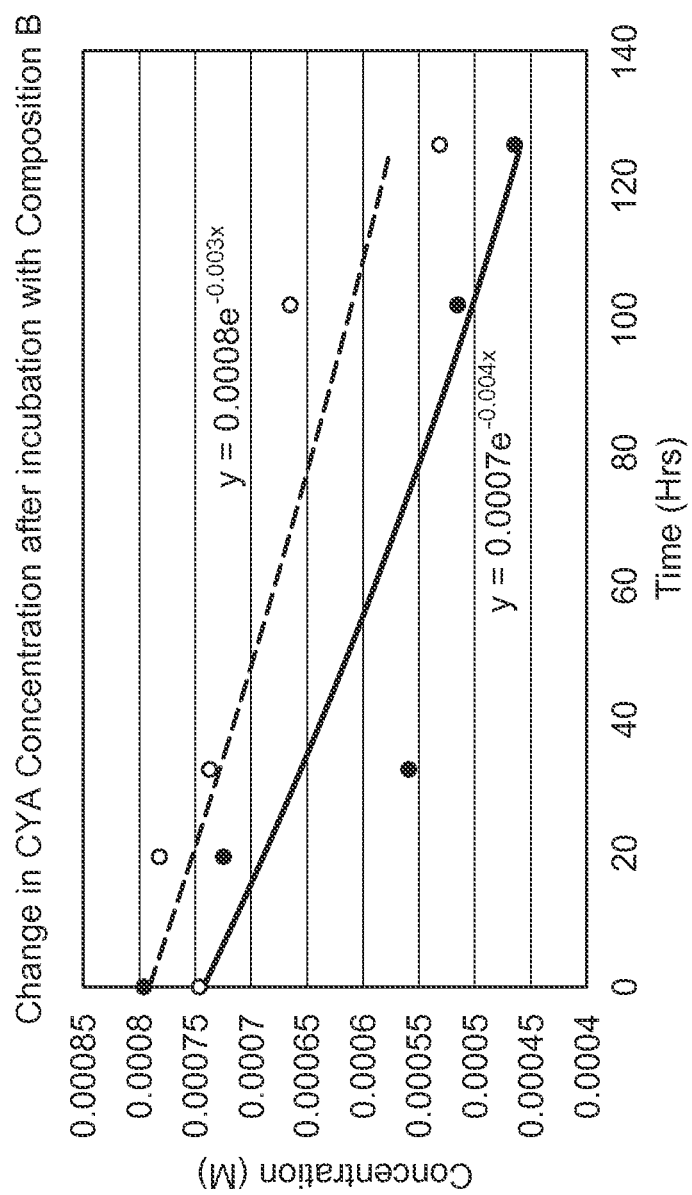
FIG. 6 illustrate that Composition B from Example 1 degrades cyanuric acid.
Figure 7:
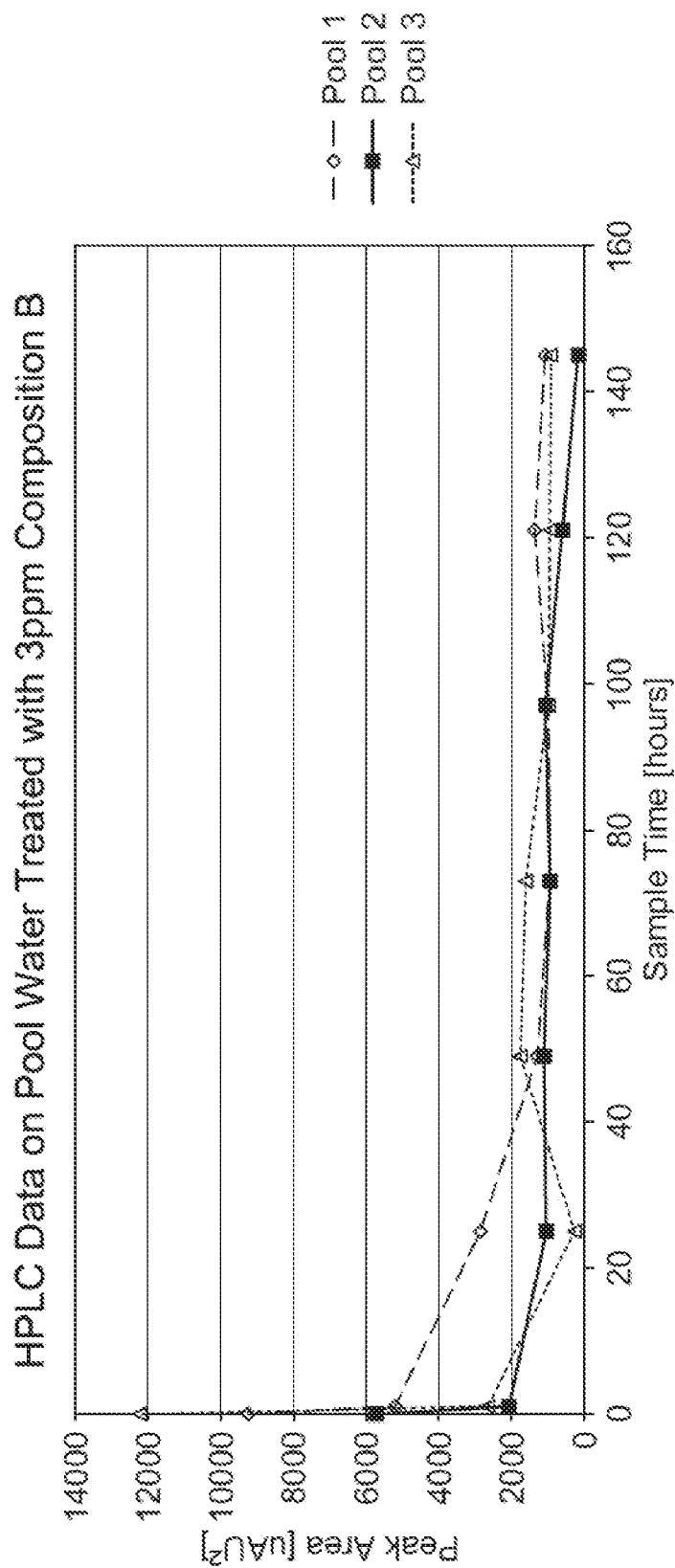
FIG. 7 illustrates that with Composition B from Example 1 degrades cyanuric acid in water from public swimming pools
Figure 8:
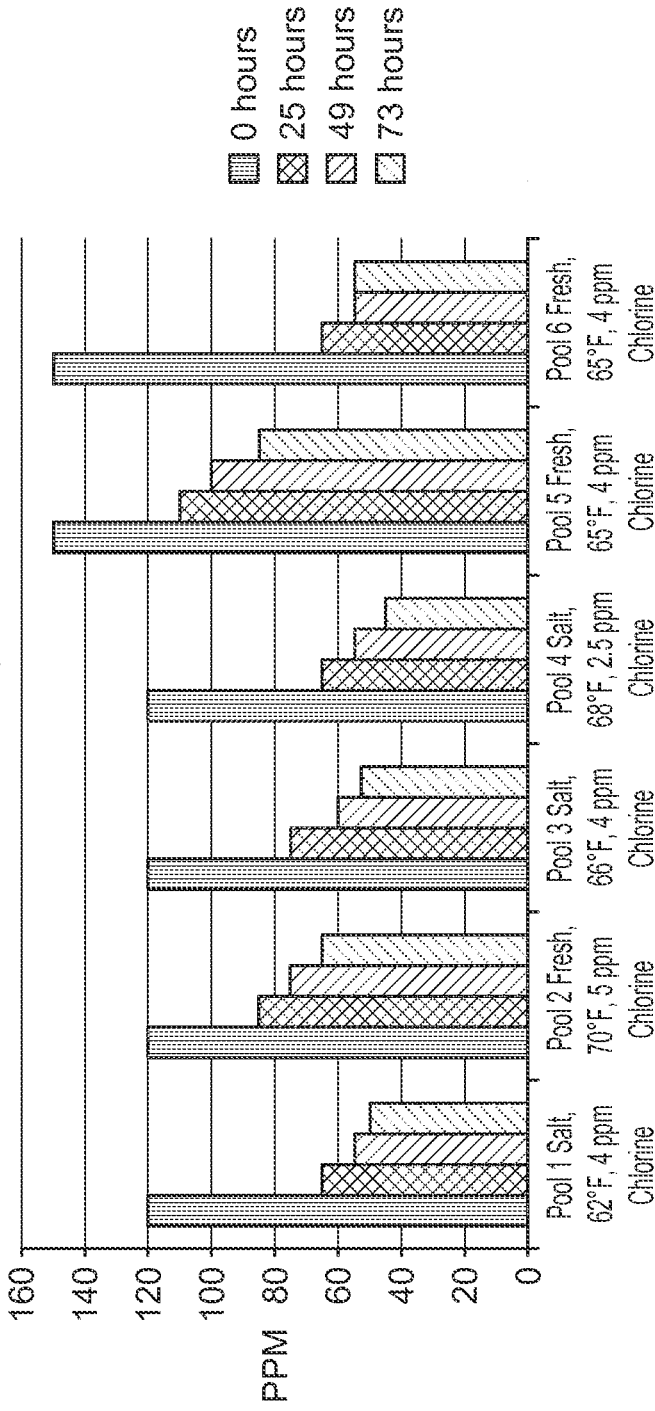
FIG. 8 illustrates that pools from southern California treated with Composition B from Example 1 have a drop in cyanuric acid concentration over time after treatment.

Compositions A and B from Example 7 were tested for their ability to degrade cyanuric acid in vitro. Stock solutions of Cyanuric acid were prepared by dissolving 100 mg cyanuric acid in 1 liter of hot autoclaved DI water. Compositions A and B were dosed at 1 gram/L into separate 100 mls aliquots of the stock cyanuric acid solutions then incubated in an incubating shaker at 30° C./150 rpm. 10 ml aliquots were pulled from each sample at times 0, 3, 6, 8, and 24 hours then frozen to shut down microbial activity. The frozen samples were analyzed by MS-MS. Results are shown in FIG. 4.

As expected, in sterile systems, addition of an oxidizable carbon source alone (Composition A) is not sufficient to cause reduction of cyanuric acid. However, in combination with select microbial species (Composition B), 65% of the initial cyanuric acid is removed after 24 hours incubation.

Example 9. In-Vivo Cyanuric Acid Reduction

Compositions A, B, and C from Example 7 were tested for their ability to reduce cyanuric acid in recreational swimming pools. For this analysis cyanuric acid levels were measured using a test kit common to the pool industry. The kit comprises a plastic tube into which a sample of pool water is added. A reagent solution comprising a low level of melamine is added to the pool water and the sample agitated for 1-2 minutes. Cyanuric acid levels are recorded visually using a dipstick calibrated between 20-100 ppm. 8 Ounces of the compositions from Example 7 were added into the skimmers of three separate pools. Results are shown below:

TABLE 6

| Pool #1 | Pool #2 | Pool #3 |
|---|---|---|
| 4.3 ppm Composition A | 3.7 ppm Composition B | 3.7 ppm Composition C |
| Pool Capacity = 14,000 gal. | Pool Capacity = 16,000 gal. | Pool Capacity = 16,000 gal. |
| 82° F. | 80° F. | 85° F. |
| pH: 7.8 | pH: 7.6 | pH: 7.6 |
| Initial CYA (cyanuric acid) level = +150 ppm | Initial CYA level = 120 ppm | Initial CYA level = 120 ppm |
| CYA level at 25 hours = 55 ppm | CYA level at 25 hours = 65 ppm | CYA level at 25 hours = 75 ppm |
| % CYA Reduction >63% | % CYA Reduction >45% | % CYA Reduction >37% |

The Compositions were further tested for their ability to reduce cyanuric acid in recreational swimming pools. Results are shown below:

TABLE 7

| POOL | TYPE | TEMPERATURE | CHLORINE | ALKALINITY | PH | CYA | FILLER | GALLONS |
|---|---|---|---|---|---|---|---|---|
| 1 | Salt water Vinyl liner | START: 55° 24 HR: 58° | START: 2.0 24 HR: 1.0 | START: 100 24 HR: 90 | START: 7.4 24 HR: 7.4 | START: 70 3 HR: N/C 24 HR: 50 | DE | 20,000 |
| 2 | Fresh water Vinyl liner | START: 55° 24 HR: 59° | START: 5 24 HR: 3.0 | START: 120 24 HR: 120 | START: 7.2 24 HR: 7.4 | START: 140-150 3 HR: 100-110 24 HR: 80 | SAND | 14,000 |
| 3 | Salt water Vinyl liner | START: 58° 24 HR: 58° 48 HR: 55° | START: 3.0 24 HR: 3.0 48 HR: 3.0 | START: 90 24 HR: 90 48 HR: 90 | START: 7.2 24 HR: 7.4 48 HR: 7.4 | START: 75-80 24 HR: 45-50 DAYS: 35-40 | | 20,000 |
| 6 | Fiber Glass | START: 65° 3 HR: 85° 26 HR: 85° 65 HR: 65° | START: 3.0 3 HR: 4.0 72 HR: 4 | START: 100 3 HR: 120 72 HR: 100 | START: 7.6 3 HR: 7.8 72 HR: 7.8 | START: 200+ 3 HR: 100 22 HR: 80-90 26 HR: 70 72 HR: 60-70 | SAND | 6,500 |
| 7 | Fiber Glass | START: 60° 3 HR: 62° 24 HR: 58° | START: 2.0 3 HR: 2.0 24 HR: 2.0 | START: 80 2 HR: 80 24 HR: 80 | START: 7.4 3 HR: 7.2 24 HR: 7.4 | START: 200+ 3 HR: N/C 24 HR: 90 48 HR: 70 | SAND | 5,000 |
| 8 | Cement | START: 58° 24 HR: 58° | START: 5 24 HR: 4 48 HR: 10 | START: 120 24 HR: 120 48 HR: 100 | START: 7.4 24 HR: 7.4 48 HR: 7.4 | START: 300+ 24 HR: 100-110 48 HR: 80-90 | SAND | 12,000 |
| 9 | Commercial Gunnite | START: 60° 21 HR: 62° 72 HR: 60° | START: 1.0 21 HR: 2.0 72 HR: 2 | START: 120 21 HR: 120 72 HR: 120 | START: 7.8 21 HR: 7.8 72 HR: 7 | START: 180 21 HR: 100 72 HR: 60 | SAND | 108,000 |

Example 10. In-Vivo Cyanuric Acid Reduction

Table 8 shows the results of cyanuric acid reduction using the compositions of the invention:

TABLE 8

| Pool Number | Location (city) | Pool size (gallons) | dosage | Initial CYA Level (PPM) | Final CYA Level (PPM) |
|---|---|---|---|---|---|
| 1 | Murrieta, CA | 10,000 | 16 Oz. | 600 | 300 |
| 2 | San Diego, CA | 30,000 | 16 Oz. | 110 | 40 |
| 3 | Murrieta, CA | 25,000 | 16 Oz. | 280 | 100 |
| 4 | Oceanside, CA | 20,000 | 8 Oz. | 100 | 30 |
| 5 | Fallbrook, CA | 35,000 | 16 Oz. | 120 | 60 |

TABLE 8-continued

| Pool Number | Location (city) | Pool size (gallons) | dosage | Initial CYA Level (PPM) | Final CYA Level (PPM) |
|---|---|---|---|---|---|
| 6 | Carlsbad, CA | 30,000 | 16 Oz. | 200 | 110 |
| 7 | Temecula, CA | 18,000 | 16 Oz. | 550 | 200 |

Example 11. In-Vivo Cyanuric Acid Reduction

Tables 9-11 show the progression of cyanuric acid reduction.

TABLE 9

| Before treatment | | | |
|---|---|---|---|
| | Fluidra Test Pool #1 | Fluidra Test Pool #2 | Fluidra Test Pool #3 |
| Cl | 0.5 | 4.5 | 9 |
| pH | 7.8 | 6.8 | 6.8 |
| Alk | 80 | 80 | 90 |
| Cyanuric Acid (CYA) | 50 | 120-140 | 140 |
| TDS | 1600 | 500 | 500 |
| Temp | 75 | 75 | 70 |
| Gallons | 5200 | 51000 | 16000 |
| Copper | 0 | 1 | 0.6 |
| BIO-CAR ADDED | 8 oz ES | 16 oz | 8 oz |

TABLE 10

| 24 hours into treatment | | | |
|---|---|---|---|
| | Fluidra Test Pool #1 | Fluidra Test Pool #2 | Fluidra Test Pool #3 |
| Cl | 0 | 5 | 9 |
| pH | 7.8 | 6.6 | 6.8 |
| Alk | 80 | 80 | 90 |
| Cyanuric Acid (CYA) | 35-40 | 90-100 | 100 |
| TDS | 1600 | 500 | 500 |
| Temp | 75 | 75 | 72 |
| Copper | 0 | 1 | 0.6 |
| Gallons | 5200 | 51000 | 16000 |

TABLE 11

| 48 hours into treatment | | | |
|---|---|---|---|
| | Fluidra Test Pool #1 | Fluidra Test Pool #2 | Fluidra Test Pool #3 |
| Cl | 0 | 5 | 9 |
| pH | 7.6 | 6.4 | 6.4 |
| Alk | 80 | 80 | 90 |
| Cyanuric Acid (CYA) | 30 | 80-90 | 90 |
| TDS | 1600 | 500 | 500 |
| Temp | 75 | 75 | 70 |
| Copper | 0 | 1 | 0.6 |
| Gallons | 5200 | 51000 | 16000 |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A composition comprising
   a. between 75-99% w/w of anhydrous dextrose or dextrose monohydrate;
   b. a mixture of *Bacillus* bacterial species comprising *Bacillus subtilis*, *Bacillus licheniformis*, *Bacillus amyloliquefaciens*, and *Bacillus pumilus* having a bacterial concentration of at least $1 \times 10^6$ colony forming units (CFU) per gram of the mixture, wherein each of the *Bacillus* species are individually fermented aerobically, dried, and ground to an average particle size of about 200 microns, and wherein the *Bacillus subtilis* comprises *Mojavensis* and *Bacillus subtilis* 34 KLB; and
   c. a mixture of *Lactobacillus* bacterial species comprising *Pediococcus acidilactici*, *Pediococcus pentosaceus*, and *Lactobacillus plantarum* having a bacterial concentration of at least $1 \times 10^6$ colony forming units (CFU) per gram of the mixture, wherein each of the *Lactobacillus* species are fermented anaerobically, dried, and ground to an average particle size of about 200 microns.

2. The composition of claim 1, wherein the bacterial species are non-pathogenic.

3. The composition of claim 1, wherein at least 15% of the *Bacillus* bacterial species are *Bacillus subtilis* 34 KLB.

4. The composition of claim 1, wherein each of the *Lactobacillus* bacterial species are present in equal amounts by weight.

5. The composition according to claim 1, wherein the composition further comprises an inorganic mineral that stimulates bacterial respiration and growth.

6. The composition according to claim 5, wherein the inorganic mineral is selected from the group consisting of disodium hydrogen phosphate, dipotassium hydrogen phosphate, sodium dihydrogen phosphate, potassium dihydrogen phosphate, sodium chloride, potassium chloride, magnesium sulfate, calcium sulfate, magnesium chloride, calcium chloride, and iron(III) chloride.

7. A method for reducing cyanuric acid concentration in a recreational water system comprising contacting a pool's filtration system with the composition of claim 1.

8. A composition comprising
   a. between 75-95% w/w of anhydrous dextrose or dextrose monohydrate;
   b. at least 1% w/w of a mixture containing *Bacillus* bacterial species comprising *Bacillus subtilis*, *Bacillus licheniformis*, *Bacillus amyloliquefaciens*, and *Bacillus pumilus*, wherein each of the *Bacillus* species are individually fermented aerobically, dried, and ground to an average particle size of about 200 microns, and wherein the *Bacillus subtilis* comprises *Mojavensis* and *Bacillus subtilis* 34 KLB; and
   c. at least 4% w/w of a mixture containing *Lactobacillus* bacterial species comprising *Pediococcus acidilactici*, *Pediococcus pentosaceus*, and *Lactobacillus plantarum*, wherein each of the *Lactobacillus* species are fermented anaerobically, dried, and ground to an average particle size of about 200 microns.

9. The composition of claim 8, wherein at least 15% of the *Bacillus* bacterial species are *Bacillus subtilis* 34 KLB.

10. The composition of claim 8, wherein each of the *Lactobacillus* bacterial species are present in equal amounts by weight.

11. The composition of claim 8, wherein the composition further comprises an inorganic mineral that stimulates bacterial respiration and growth.

12. The composition of claim 11, wherein the inorganic mineral is selected from the group consisting of disodium hydrogen phosphate, dipotassium hydrogen phosphate, sodium dihydrogen phosphate, potassium dihydrogen phosphate, sodium chloride, potassium chloride, magnesium sulfate, calcium sulfate, magnesium chloride, calcium chloride, and iron(III) chloride.

13. A method for reducing cyanuric acid concentration in a recreational water system comprising contacting a pool's filtration system with the composition of claim 8.

* * * * *